United States Patent [19]

Gers-Barlag et al.

[11] Patent Number: 5,658,556
[45] Date of Patent: Aug. 19, 1997

[54] COSMETIC OR DERMATOLOGICAL PREPARATIONS COMPRISING HYDROPHOBICIZED INORGANIC PIGMENTS FOR PRESERVING THE UROCANINIC ACID STATE OF THE SKIN

[75] Inventors: Heinrich Gers-Barlag, Kummerfeld; Sabine Schulz, Hamburg; Beate Uhlmann, Hamburg; Ulrich Hintze, Hamburg; Robert Schmucker, Hamburg, all of Germany

[73] Assignee: Beiersdorf Aktiengesellschaft, Hamburg, Germany

[21] Appl. No.: 515,759

[22] Filed: Aug. 15, 1995

[30] Foreign Application Priority Data

Aug. 19, 1994 [DE] Germany .................. 44 29 468.9

[51] Int. Cl.$^6$ .................. A61K 7/00; A61K 7/40
[52] U.S. Cl. .................. 424/63; 424/59; 424/401
[58] Field of Search .................. 424/59, 401, 63

[56] References Cited

U.S. PATENT DOCUMENTS 5,455,036  10/1995  Stab et al. .................. 424/401
5,494,676  2/1996   Stab et al. .................. 424/401

Primary Examiner—Salle M. Gardner
Attorney, Agent, or Firm—Sprung Horn Kramer & Woods

[57] ABSTRACT

Use of one or more hydrophobicized, pharmaceutically or cosmetically acceptable inorganic pigments in cosmetic or dermatological preparations for preventing

- leaching out or washing off of the skin's cis- or trans-urocaninic acid from the human skin, caused by the action of water, or
- leaching out or washing off of cis- or trans-urocaninic acid which has been applied artificially to the skin, from the human skin caused by the action of water.

8 Claims, No Drawings

COSMETIC OR DERMATOLOGICAL PREPARATIONS COMPRISING HYDROPHOBICIZED INORGANIC PIGMENTS FOR PRESERVING THE UROCANINIC ACID STATE OF THE SKIN

The present invention relates to cosmetic or dermatological preparations comprising hydrophobized inorganic pigments. In some embodiments, the present invention also relates to cosmetic cleansers. In further embodiments, the present invention relates to preparations for protecting the skin against UV radiation. The invention furthermore relates to dermatological preparations which preserve and improve the immunological state of human skin. Finally, the invention relates to preparations which reduce or prevent the loss from the skin of certain skin constituents when washing the body.

Skin care is to be understood as meaning mainly the strengthening or restoration of the skin's natural function as a barrier against environmental factors (for example dirt, chemicals, microorganisms) and against the loss of substances which make up the body (for example water, natural fats, electrolytes).

Interference with this function can result in greater absorption of toxic or allergenic substances or infection with microorganisms and, as a consequence, toxic or allergic skin reactions.

Another aim of skin care is to compensate for the skin's loss of fats and of water, which is caused by daily washing. This is particularly important when the natural regeneration capacity is insufficient. Furthermore, skin care products are intended to protect against environmental factors, in particular sun and wind, and to delay signs of skin ageing.

cis-Urocaninic acid (also termed cis-urocanic acid or cis-4-imidazolylacrylic acid) is characterized by the following structural formula:

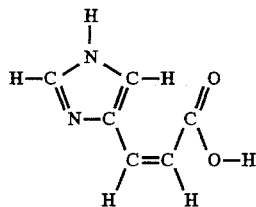

Its empirical formula is $C_6H_6N_2O_2$ and its molecular weight 138.12. cis-Urocaninic acid is formed, for example, by the UV irradiation of the trans isomer, which can be found in the human skin and also in sweat.

Trans-Urocaninic acid is characterized by the following structural formula:

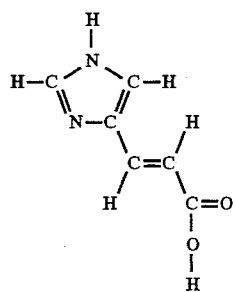

The empirical formula of trans-urocaninic acid is $C_6H_6N_2O_2$ and its molecular weight 138.12, and it can be found in the human skin and also in sweat.

If the term "urocaninic acid" is used within the scope of the disclosure produced herewith without any indication of the isomer in question, this is intended to embrace the cis and trans isomer, and also any mixtures of the two isomers.

German Offenlegungsschrift 41 21 030 demonstrates that urocaninic acid has an antiphlogistic action, alleviates the sequelae of allergic reactions and prevents allergic reactions to a high degree.

Due to its antiphlogistic and antiallergic potential, urocaninic acid is active against psoriasis, neurodermitis and contact dermatitis and also autoimmune diseases, such as, for example, vitiligo, pruritus, alopecia areata, ichthyosis and atopy, where a similar mechanism of action exists.

Conventional preparations were incapable of preventing the skin's urocaninic acid to be leached out, or washed off, when coming into contact with water and/or surfactants, or when sweating. Equally, conventional preparations comprising urocaninic acid were only capable of improving the urocaninic acid state of the skin slightly, at best, but themselves not capable of restoring the original state. As yet, this state could only be reached after the individual regeneration time of the individual in question had elapsed.

Skin care preparations are usually in the form of creams, lotions, milks, ointments, ointment bases, oils, tinctures, sticks, spray formulations and the like.

Customary cosmetic preparations are, for example, suntan compositions. The use of trans-urocaninic acid as a suntan composition is also known.

It is generally known that the ultraviolet portion of sunlight has a damaging effect on the skin. While rays with a wavelength of less than 290 nm (the so-called UVC range) are absorbed from the ozone layer in the earth's atmosphere, rays in the range of between 290 nm and 320 nm, the so-called UVB range, cause erythema, simple sunburn or even more or less pronounced burning of the skin.

The maximum activity of the sunlight for causing erythema is to be considered in the narrower range around 308 nm.

A large number of compounds are known to protect against UVB radiation, most of these compounds being derivatives of 3-benzylidenecamphor, 4-aminobenzoic acid, cinnamic acid, salicylic acid, benzophenone and also 2-phenylbenzimidazole.

UV filters are also important for the wavelength range between approximately 320 and 400 nm, the so-called UVA range, since those rays too are capable of causing damage. For example, it has been proven that UVA radiation results in damage to the elastic and collagenic fibres of connecting tissue, which causes premature ageing of the skin and is considered as the cause of a large number of phototoxic and photoallergic reactions. The damaging effect of UVB radiation can be enhanced by UVA radiation.

In addition, UV radiation, however, can result in photochemical reactions, the photochemical reaction products engaging in the metabolism of the skin and cells.

Such photochemical reaction products are mainly free-radical compounds, for example hydroxyl radicals, hydroperoxy radicals and superoxide ions. In addition, undefined free-radical photochemical reaction products, which are formed in the skin itself, can trigger uncontrolled secondary reactions due to their high reactivity. However even singlet oxygen, a non-free-radical, excited state of the oxygen molecule, may be formed on UV irradiation, as are short-lived epoxides and a large number of other substances. Singlet oxygen, for example, differs from the normally existing triplet oxygen (free-radical ground state) by its increased reactivity. However, excited, reactive (free-radical) triplet states of the oxygen molecule exist as well.

To prevent these reactions, antioxidants and/or free-radical scavengers may additionally be incorporated into the cosmetic or dermatological formulations.

UV absorbers, or UV reflectors, are most inorganic pigments whose use in cosmetics for protecting the skin against UV rays is known. They are oxides of titanium, zinc, iron, zirconium, silicon, manganese, aluminium, cerium and mixtures of these, and also modifications.

Even though advantageous cosmetic or dermatological preparations for protecting the skin against harmful sequelae after exposure to UV light certainly exist, the fact that the preparations are not, or insufficiently, waterproof is a frequently observed disadvantage.

Sun protection preparations are particularly frequently used, and required, on beaches or in open-air swimming pools. It is then desirable that the sun protection formulation is largely waterproof, i.e. that it is not washed off from the skin, or to a small extent only.

Higher sun protection factors, that is to say those above SPF 15, are generally only achieved by using large amounts of UV filters. If it is intended for a suntan product to retain a high sun protection factor even after bathing, then the UV filter, in particular, must remain on the skin.

Having to reapply the suntan product after bathing is already a nuisance in itself. When bathing, the use of a non-waterproof sun protection formulation may in certain circumstances even be irresponsible and damaging to the skin since water absorbs light in the UVA and UVB range poorly, which is why it does not represent sizeable UV protection, not even for submerged parts of the skin.

Substances which are conventionally used in the prior art for waterproof sun protection formulations are non-water-soluble UV filters, hydrophobic raw materials (for example silicone oils at high concentrations) and/or film formers, in particular high-molecular-weight compounds pounds (for example PVP/hexadecene copolymers). Here, barriers are built up between the UV filters on the skin and the water.

The disadvantage is that diffusion of the filters into the water can be delayed, but not completely prevented. This is why such products can lose their protective action to a high degree upon prolonged bathing. However, sun protection can even be reduced considerably by normal perspiration or wiping off this sweat and the sun protection substances which are dissolved, or partially dissolved, therein in particular the skin's own, but also the artificially applied urocaninic acid.

Even if surfactant-free water suffices to reduce the skin's content of urocaninic acid, this is even more the case when additional surfactants are present, i.e. in the presence of cleansing formulations.

Cosmetic cleansing preparations are mainly surface-active substances or substance mixtures which are offered to the consumer in a variety of preparations. Such preparations are generally distinguished by a more or less high water content, but may also be in virtually water-free form, for example as a concentrate.

In general, there is no, or virtually no, difference between preparations intended for showering and those for baths, apart from the fact that, as shower preparations, products having a higher viscosity are preferred which do not run off the hand after having been dispensed from the container. In the case of bath preparations, this is of less practical importance.

Even when simply bathing in water without adding surfactants, the horny layer of the skin first swells, the degree of swelling depending, for example, on the duration of the bath and the temperature. At the same time, water-soluble substances, for example water-soluble dirt components, but also the skin's substances which are responsible for the water-bonding capacity of the horny layer, are washed off or leached out. Due to the skin's surfactants, the skin's oils are also dissolved and leached out to some extent. This results in initial swelling followed by noticeable dehydration of the skin, which can be made even worse by additives which act as detergents. In particular the skin's urocaninic acid can be readily leached out of the skin since it is highly hydrophilic.

In healthy skin, these processes are generally of no importance since the protective mechanisms of the skin can readily compensate for such slightly adverse effects on the upper layers of the skin. However, even in the case of non-pathological deviations from the normal state, for example due to wear or irritation caused by environmental factors, light-induced damage, ageing skin and the like, the protective mechanism of the skin surface is disturbed. Under certain circumstances, it is then no longer itself capable of performing its task and has to be regenerated by external measures.

Cleansing preparations are known per se. They are essentially surface-active substances or substance mixtures which are offered to the consumer in the form of various preparations.

Preparations of this type are, for example, bubble baths and shower preparations, solid and liquid soaps or so-called "syndets" (synthetic detergents), shampoos, hand-washing pastes, washing preparations for feminine hygiene, special cleansers for infants, and the like.

Surface-active substances—of which the alkali metal salts of the higher fatty acids, i.e. the traditional soaps, are known best—are amphiphilic substances which are capable of emulsifying organic unpolar substances in water.

These substances not only remove dirt from skin and hair, but also irritate the skin and mucus membranes to a greater or lesser extent, depending on the choice of surfactant or surfactant mixture.

However, the prior art also knows various types of low-water or water-free oil-bath preparations, it being possible for the properties of the fatty, or oily, phase to be varied by adding surface-active substances. Depending on the nature and the amount of the components chosen, preparations can be formulated which form, on the surface of the bath water, either spreading oil films, oil-in-water systems or else total solubilizates. The formulations which are possible may be foaming, but also low-foam or non-foaming.

In the case of oil-bath or oil-cream-bath preparations, the mode of action of such preparations is generally limited to refatting or superfatting the uppermost layers of the skin with the amount of fat, or more, which has been lost. However, compositions which comprise active compound are also known.

It was therefore an object of the present invention to remedy all these shortcomings. In particular, it was an object of the invention to provide preparations which, whether or not an additional urocaninic acid content is admixed with them, guarantee that, after contact with water, the urocaninic acid state of the skin is adversely affected as little as possible, or, in the case of an acute deficit of urocaninic acid, a nearly physiological urocaninic acid state is achieved.

Surprisingly, these objects are achieved by the use of one or more hydrophobicized, pharmaceutically or cosmetically acceptable inorganic pigments in cosmetic or dermatological preparations for preventing leaching out or washing off of the skin's cis- or trans-urocaninic acid from the human skin, caused by the action of water, or leaching out or washing off of cis- or trans-urocaninic acid which has been applied artificially to the skin, from the human skin, caused by the action of water.

According to the invention, it is advantageous to choose urocaninic-acid-free preparations. If appropriate, however, it may also be advantageous to use a cis- and/or trans-urocaninic acid content in the preparations according to the invention.

As a rule, medicinal topical compositions comprise an effective concentration of one or more medicaments. For the sake of simplicity, the legal regulations of the Federal Republic of Germany are referred to in order to distinguish clearly between cosmetic and medicinal use and between the corresponding products (for example Kosmetikverordnung [Cosmetics Decree], Lebens-mittel- and Arzneimittelgesetz [Food and Drug Act]).

While M. Schmidt and S. G. Steinemann describe, in "XPS studies of amino acids adsorbed on titanium dioxide surfaces", Fresenius' Journal of Analytical Chemistry (1991) 341, pp. 412–415 that certain amino acids are readily adsorbed by the surface of titanium dioxide particles, this paper suggests in no way the present invention and its advantageous properties. Moreover, $TiO_2$, which is cited in the above paper, is not hydrophobic.

It is furthermore surprising that it is precisely the hydrophobized inorganic pigments which have the advantageous properties according to the invention, since urocaninic acid must certainly be considered to be a hydrophilic substance.

Finally, it is surprising that it is immaterial for practical purposes whether the preparations according to the invention with regard to the formulation itself are to be considered as "waterproof" (i.e., for example, using a pronounced content of water-insoluble film formers) or as "non-waterproof" (i.e., for example, without such a content). According to the invention, the urocaninic acid state of the skin is only marginally worse after the provocative use of water when no film-forming preparations are used than when such film-forming preparations are used.

Cosmetic and dermatological preparations according to the invention preferably comprise inorganic pigments based on metal oxides and/or other metal compounds which are sparingly soluble or insoluble in water, in particular oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$), cerium (for example $Ce_2O_3$) mixed oxides of these metals, and mixtures of such oxides. Particularly preferred pigments are $TiO_2$-based.

A prerequisite for the potential use of inorganic pigments for the purposes according to the invention is, naturally, the cosmetic or dermatological acceptability of the substances on which they are based.

The modifications in which such metal oxides are present are essentially immaterial for the present invention. For example, $TiO_2$ can be found naturally in three main modifications (rutile, anatase and brookite), all of which are, basically, equally suitable. The same applies analogously to modifications of iron oxides and the like.

It is advantageous to choose a particle diameter of the pigments used which is less than 100 nm.

According to the invention, the inorganic pigments are in hydrophobic form, i.e. they have been treated so that their surface is water-repellent. This surface treatment may consist in providing the pigments with a thin hydrophobic layer by methode known per se.

In one of these processes, the hydrophobic surface layer is produced following the reaction

$n$ and $m$ are any stoichiometric parameters, R and R' are the desired organic radicals. Advantageous hydrophobicized pigments are, for example, those which have been prepared in analogy to U.S. Pat. No. 4,514,231.

Advantageous $TiO_2$ pigments are commercially available for example under the trade names T 805 (DEGUSSA) or M 262 (KEMIRA) or M 160 (KEMIRA) or MT 100 T (TAYCA).

Advantageous $SiO_2$ pigments can be selected from the series of the hydrophobic pigments sold under the trade names AEROSIL (DEGUSSA), for example AEROSIL R 812 or AEROSIL R 972.

The preparations according to the invention are manufactured in accordance with the customary procedures, with which the expert is familiar. The preparations according to the invention are advantageously in the form of emulsions, preferably O/W emulsions. However, it is also possible and, if appropriate, advantageous according to the invention, to choose other types of formulations, for example hydrodispersions, gels, oils, multiple emulsions, for example in the form of W/O/W or O/W/O emulsions, water-free ointment or ointment bases, and the like. Furthermore, washing preparations, such as, for example, shampoos, but in particular oil baths, oil cream baths and shower oils, represent extremely advantageous embodiments of the present invention.

In simple emulsions, the one phase contains finely dispersed droplets of the other phase, enclosed by an emulsifier shell (water droplets in W/O or lipid vesicles in O/W emulsions). In a multiple emulsion (second-degree emulsion), in contrast, more finely dispersed droplets of the first phase are emulsified in such droplets. These droplets, in turn, can also contain even more finely dispersed droplets (multiple third-degree degree emulsion) and so on.

As the simple emulsions are termed W/O or O/W emulsions (Water-in-Oil or Oil-in-Water), the multiple emulsions are therefore W/O/W, O/W/O, O/W/O/W, W/O/W/O emulsions and so on.

Hydrodispersions are dispersions of a liquid, semi-solid or solid inner (discontinuous) lipid phase in an outer aqueous (continuous) phase.

In contrast to O/W emulsions, which are distinguished by a similar phase arrangement, hydrodispersions are, however, essentially free from emulsifiers. Hydrodispersions are metastable systems, as are, by the way, emulsions, and tend to change gradually to a state of two discrete phases which are interconnected. In emulsions, the choice of a suitable emulsifier prevents phase separation.

In the case of hydrodispersions of a liquid lipid phase in an outer aqueous phase, the stability of such a system can be guaranteed for example by building up a gel skeleton in the aqueous phase in which the lipid droplets are stably suspended.

It is possible and advantageous to add the hydrophobic inorganic pigment(s), and, if desired, the urocaninic acid to the emulsion mixture at any point in time when preparing the emulsion. Pigment or pigments, and, if desired, the urocaninic acid can be added to the emulsion mixture separately or already combined with each other.

Furthermore, particularly advantageous preparations are obtained when the active compounds according to the invention are combined with antioxidants. The preparations advantageously comprise according to the invention one or more antioxidants. As antioxidants which are favourable but are to be used optionally, all antioxidants are used which are suitable or customary for cosmetic and/or dermatological purposes.

The antioxidants are particularly advantageously selected from the group consisting of amino acids (for example glycine, histidine, tyrosine, tryptophan) and their derivatives, imidazoles and their derivatives, peptides, D,L-carnosine, D-carnosine, L-carnosine and derivatives thereof (for example anserine), carotenoids, carotenes (for example α-carotene, β-carotene, lycopine) and their derivatives, lipoic acid and its derivatives (for example dihydrolipoic acid), aurothioglucose, propylthiouracil and other thiols (for example thioredoxine, glutathione, cysteine, cystine, cystamine and their glycosyl, N-acetyl, methyl, ethyl, propyl, amyl, butyl and lauryl, palmitoyl, oleyl, gamma-linoleyl, cholesteryl and glyceryl esters) and their salts, dilauryl dithiodipropionate, distearyl thiodipropionate, thiodipropionic acid and its derivatives (esters, ethers, peptides, lipids, nucleotides, nucleosides and salts) and sulphoximine compounds (for example buthionine sulphoximines, homocysteine sulphoximine, buthionine sulphones, and penta-, hexa-, and heptathionine sulphoximine) at very low acceptable dosages (for example pmol to µmol/kg), further (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and their derivatives, unsaturated fatty acids and their derivatives (for example gamma-linolenic acid, linoleic acid, oleic acid), folic acid and its derivatives, ubiquinone and ubiquinol and their derivatives, vitamin C and derivatives (for example ascorbyl palmitates, Mg ascorbyl phosphates, ascorbyl acetates), tocopherols and derivatives (for example vitamin E acetate), vitamin A and derivatives (vitamin A palmitate) and coniferyl benzoate from benzoic resin, rutinic acid and its derivatives, ferulic acid and its derivatives, butylated hydroxytoluene, butylated hydroxyanisole, furalglucitol, nordihydroguaiac resin acid, nordihydroguaiaretic acid, trihydroxybutyrophenone, uric acid and its derivatives, mannose and its derivatives, zinc and its derivatives (for example ZnO, ZnSO$_4$), selenium and its derivatives (for example selenium methionine), stilbenes and their derivatives (for example stilbene oxide, trans-stilbene oxide) and the derivatives of the abovementioned active compounds which are suitable according to the invention (salts, esters, ethers, sugars, nucleotides, nucleosides, peptides and lipids).

Substances which can be employed particularly advantageously in the sense of the present invention are oil-soluble antioxidants.

The amount of antioxidants (one or more compounds) in the preparations is preferably 0.001 to 30% by weight, particularly preferably 0.05–20% by weight, especially 1–10% by weight, based on the total weight of the preparation.

If vitamin E and/or its derivatives is/are the antioxidant (s), it is advantageous to select their respective concentrations from the range 0.001–10% by weight, based on the total weight of the formulation.

If vitamin A, or vitamin A derivatives or carotenes, or their derivatives, is/are the antioxidant(s), it is advantageous to choose their respective concentrations from the range of 0.001–10% by weight, based on the total weight of the formulation.

If desired, it is advantageous to incorporate urocaninic acid into the preparations according to the invention, preferably in concentrations of 0.00001 mg/ml–60 mg/ml, based on the total volume of the preparations. Preferred preparations contain concentrations of 0.01 mg/ml–2.0 mg/ml, in particular 0.05 mg/ml–1.0 mg/ml, in each case based on the total volume of the preparations.

The formulations according to the invention which comprise urocaninic acid are advantageously in the form of emulsions, preferably O/W emulsions. However, it is also possible and, if appropriate, advantageous according to the invention to choose other types of formulations, for example hydrodispersions, gels, oils, multiple emulsions, for example in the form of W/O/W or O/W/O emulsions, water-free ointments or ointment bases and the like. Other highly advantageous embodiments of the present invention are washing preparations such as, for example, shampoos, oil baths, oil cream baths and shower oils. It has furthermore proved to be advantageous to incorporate aqueous or alcoholic/aqueous or alcoholic or acetonic/aqueous or acetonic or acetonic/alcoholic solutions of urocaninic acid into the formulations.

It is furthermore advantageous to incorporate, into the compositions, auxiliaries and/or additives which improve the stability of the urocaninic acid or its derivatives, or which improve or alter the quality of the compositions regarding their formulation.

The cosmetic preparations according to the invention can comprise cosmetic auxiliaries as they are conventionally used in such preparations, for example preservatives, bactericides, deodorant substances, antiperspirants, insect repellents, vitamins, antifoams, colourants, pigments with a colourant action, thickeners, plasticizers, moisturizers and/or humectants, fats, oils, waxes or any other customary components of a cosmetic formulation, such as alcohols, polyols, polymers, foam stabilizers, electrolytes, organic solvents or silicone derivatives.

The preparations according to the invention can furthermore advantageously comprise substances which absorb UV radiation in the UBV range, the total amount of filter substances being, for example, 0.1% by weight to 30% by weight, preferably 0.5 to 10% by weight, especially 1 to 6% by weight, based on the total weight of the preparation.

The pH of the preparations according to the invention can advantageously be brought into the acidic range, a pH range of 3.5–7 being preferred and of 4–5 particularly preferred.

Preparations according to the invention can also advantageously be used as suntan compositions. Furthermore, it is highly advantageous to use preparations according to the invention for all sports, in particular those which cause perspiration.

Advantageous emulsions according to the invention are, for example, in the form of a suntan cream or a suntan lotion and comprise, for example, the above-mentioned fats, oils, waxes and other lipids as well as water and an emulsifer as it is conventionally used for this type of formulation.

The UVB filters can be oil-soluble or water-soluble. Examples of advantageous oil-soluble UVB filters are:

3-benzylidenecamphor derivatives, preferably 3-(4-methylbenzylidene)camphor, 3-benzylidenecamphor;

4-aminobenzoic acid derivatives, preferably 2-ethylhexyl 4-(dimethylamino)benzoate, amyl 4-(dimethylamino) benzoate;

cinnamic acid esters, preferably 2-ethylhexyl 4-methoxycinnamate, isopentyl 4-methoxycinnamate;

salicylic acid esters, preferably 2-ethylhexyl salicylate, 4-isopropylbenzyl salicylate, homomenthyl salicylate;

benzophenone derivatives, preferably 2-hydroxy-4-methoxybenzophenone, 2-hydroxy-4-methoxy-4'-methylbenzophenone, 2,2'-dihydroxy-4-methoxybenzophenone;

benzalmalonic acid esters, preferably di(2-ethylhexyl) 4-methoxybenzalmalonate;

2,4,6-trianilino-(p-carbo-2'-ethyl-1'-hexyloxy)-1,3,5-triazine.

Examples of advantageous water-soluble UVB filters are:

salts of 2-phenylbenzimidazole-5-sulphonic acid, such as its sodium, potassium or triethanolammonium salt, and the sulphonic acid itself;

sulphonic acid derivatives of benzophenones, preferably 2-hydroxy-4-methoxybenzophenone-5-sulphonic acid and its salts;

sulphonic acid derivatives of 3-benzylidenecamphor, such as, for example 4-(2-oxo-3-bornylidenemethyl) benzenesulphonic acid, 2-methyl-5-(2-oxo-3-bornylidenemethyl)sulphonic acid and their salts.

The preparations according to the invention can advantageously furthermore comprise substances which absorb UV radiation in the UVA range. UVA filters which can be used advantageously according to the invention are, for example, dibenzoylmethane derivatives, in particular 1-(4'-tert-butylphenyl)-3-(4'-methoxyphenyl)propane-1,3-dione and 1-phenyl-3-(4'-isopropylphenyl)propane-1,3-dione.

The total amount of UVA filters can advantageously be 0.1% by weight to 30% by weight, preferably 0.5 to 10% by weight, especially 1 to 6% by weight, based on the total weight of the preparation.

Also advantageous are those cosmetic and dermatological preparations which are in the form of a suntan composition, a before-sun or after-sun product. These advantageously additionally comprise at least one UVA filter and/or at least one UVB filter.

Particularly advantageous are furthermore also those cosmetic and dermatological preparations which are in the form of a suntan composition, a before-sun or after-sun product and which additionally to the UVA filter(s) and/or the UVB filter(s) comprise one or more antioxidants.

The total amount Of antioxidants can advantageously be 0.1% by weight to 30% by weight, preferably 0.5 to 10% by weight, especially 1 to 6% by weight, based on the total weight of the preparation.

Cosmetic cleansers according to the invention can comprise anionic, non-anionic and/or amphoteric surfactants, for example conventional soaps, such as fatty acid salts of sodium, alkyl sulphates, alkyl ether sulphates, alkane and alkylbenzenesulphonates, sulphoacetates, sulphobetaines, sarcosinates, amidosulphobetaines, sulphosuccinates, sulphosuccinic monoesters, alkyl ether carboxylates, protein/fatty acid condensates, alkylbetaines and amidobetaines, fatty acid alkanolamides and polyglycol ether derivatives.

Advantageous according to the invention are cleansing preparations in the form of an oil bath, an oil cream bath or, particularly advantageous, a shower oil. Such preparations are distinguished by the fact that they are essentially composed of oil components and surfactants and are essentially water-free or contain only small amounts of water.

Preferred shower oils are distinguished by a content of not more than 55% by weight, based on the total weight of the preparations, of one or more surfactants selected from the group consisting of fatty alcohol ethoxylates, fatty alcohol sulphates, fatty alcohol sulphate amides, fatty alcohol ether sulphates, fatty alcohol ether sulphate amides, fatty acid monoethanolamides, fatty acid diethanolamides, and a content of not less than 45% by weight, based on the total weight of the preparations, of one or more oil components selected from the group of the oils with a high content of triglycerides of saturated and/or unsaturated, branched and/or unbranched fatty acids, or comprising exclusively such triglycerides, furthermore comprising hydrophobicized inorganic pigments and, if appropriate, other cosmetic or pharmaceutical auxiliaries, additives and/or active compounds, in which case the preparations are then preferably essentially free from water.

The fatty alcohol sulphates or fatty alcohol ether sulphates to be used expediently according to the invention advantageously have the following structure:

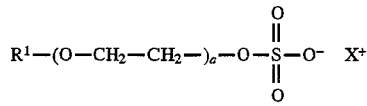

Here, a can assume values of from 0 to 10, advantageously 1 to 5. $R^1$ is selected from the group of the branched and unbranched alkyl groups having 6 to 24 carbon atoms.

$X^+$ is selected from the group of the alkali metal ions and from the group of the ammonium ions which are substituted by one or more alkyl and/or one or more hydroxyalkyl radicals.

The fatty alcohol sulphate amides or fatty alcohol ether sulphate amides to be used expediently according to the invention advantageously have the following structure:

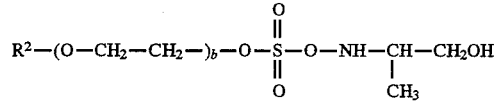

Here, b can assume values of from 0 to 10, advantageously 1 to 5. $R^2$ is selected from the group of the branched and unbranched alkyl groups having 6 to 24 carbon atoms.

The preferred fatty alcohol ether sulphate is MIPA laureth sulphate.

The fatty alcohol ethoxylates to be used expediently according to the invention advantageously have the following structure:

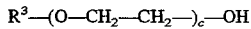

Here, c can assume values from 1 to 45, preferably 1 to 10. $R^3$ is selected from the group of the branched and unbranched alkyl groups having 6 to 24 carbon atoms.

The preferred fatty alcohol ethoxylate is laureth-4.

The fatty acid mono- or diethanolamides to be used expediently according to the invention advantageously have the following structures:

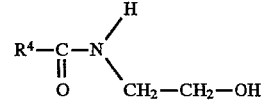

or

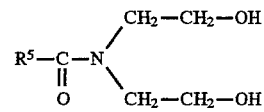

Here, $R^4$ and $R^5$ are selected from the group of the branched and unbranched alkyl groups and/or alkenyl groups having 6 to 24 carbon atoms.

The preferred fatty acid diethanolamide is coconut fatty acid diethanolamide (Cocamide DEA). Natural coconut fatty acid contains, as essential components, 44–51% by weight of lauric acid, 13–18% by weight of myristic acid, 8–10% by weight of palmitic acid, 6–9% by weight of caprylic acid, 6–10% by weight of capric acid, 5–8% by weight of oleic acid, 1–3% by weight of stearic acid, 0–2% by weight of linoleic acid and 0–1% by weight of caproic acid.

It is very particularly preferred to employ mixtures of MIPA laureth sulphate, laureth-4 and coconut fatty acid diethanolamide. Such mixtures are available, for example, by the name of ZETESOL(R) 100 from Zschimmer & Schwarz Chemische Fabriken, Lahnstein/Rhine, or TEXAPON(R) WW 99 from Henkel KGaA, Düsseldorf.

The oils according to the invention are preferably selected from the group of triglycerides of the following structure:

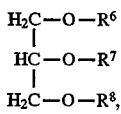

where $R^6$, $R^7$ and $R^8$ independently of one another are selected from the group of the branched and unbranched alkylcarboxyl or alkenylcarboxyl groups having 12 to 24 carbon atoms. If appropriate, it is advantageous for one or more aliphatic hydrogen atoms of the alkylcarboxyl or alkenylcarboxyl groups to be substituted by hydroxyl groups.

It is especially advantageous for $R^6$, $R^7$ and/or $R^8$ to have 16 to 20 carbon atoms and to be selected from the group of the mono- to triunsaturated carboxylic acid radicals.

If $R^6$, $R^7$ and/or $R^8$ have hydroxyl groups, the preferred alkenylcarboxyl radical is the ricinoleic acid radical.

It is particularly advantageous to select the oils according to the invention from the group consisting of soya oil, sunflower oil, wheatgerm oil and castor oil.

Preferred preparations comprise 0 to 60% by weight of soya oil, 0 to 60% by weight of wheatgerm oil and 0 to 60% by weight of sunflower oil, with the proviso that the total of the individual concentrations of these oils amounts to 30–60% by weight, furthermore castor oil at a concentration of 5–25% by weight, and these concentrations in each case being based on the total weight of the preparations.

The shower oils optionally comprise, in addition to the abovementioned surfactants, the additives which are customary in cosmetics or in pharmaceutical formulation technology, for example perfume, thickener, colourants, deodorants, antimicrobial substances, refatting agents, complexing agents and sequestering agents, pearlescent agents, plant extracts, vitamins, active compounds and the like.

It is especially advantageous to select thickeners from the group of the polyoxyethylene/polyoxypropylene block copolymers. Such block copolymers are known under the name "poloxamers" and are distinguished by the following structure:

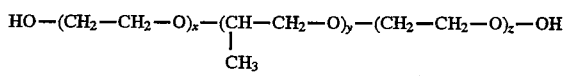

Here, x advantageously assumes values of between 2 and 20. y advantageously assumes values of between 10 and 50. z advantageously assumes values of between 2 and 20.

If it is intended for the preparations according to the present invention to comprise other surfactants in addition to the surfactants according to the invention, it is preferred to choose their concentration at not more than 5% by weight based on the weight of the total composition.

According to the invention, suitable antioxidants are all those antioxidants which are suitable or customary for cosmetics and/or dermatological purposes.

The examples will present advantageous embodiments of the present invention:

EXAMPLE 1

Sun cream, O/W, sun protection factor 20

| | % by weight |
|---|---|
| cyclomethicone | 3.00 |
| glyceryl stearate + PEG-30 stearate | 2.00 |
| wool wax alcohol | 0.10 |
| glyceryl stearate | 3.00 |
| isopropyl palmitate | 2.00 |
| octyldodecanol | 1.00 |
| $C_{12-15}$alkyl benzoate | 2.00 |
| glycerol | 3.00 |
| cetyl alcohol | 3.00 |
| myristyl myristate | 2.00 |
| octyl methoxycinnamate | 4.50 |
| butylmethoxydibenzoylmethane | 2.00 |
| phenylbenzimidazolesulphonic acid | 3.00 |
| tocopheryl acetate | 0.50 |
| EDTA solution (20%) | 0.50 |
| NaOH (45%) | q.s. |
| ethyl alcohol | 4.00 |
| preservative | q.s. |
| perfume | q.s. |
| hydrophobic $TiO_2$ | 2.00 |
| fully demineralized water | to 100.00 |

EXAMPLE 2

Sun cream, O/W, sun protection factor 8

| | % by weight |
|---|---|
| cyclomethicone | 3.00 |
| glyceryl stearate + PEG-30 stearate | 2.00 |
| glyceryl stearate | 3.00 |
| isopropyl palmitate | 2.00 |
| octyldodecanol | 3.00 |
| glycerol | 3.00 |
| cetyl alcohol | 3.00 |
| phenylbenzimidazolesulphonic acid | 1.00 |
| octyl methoxycinnamate | 5.00 |
| butylmethoxydibenzoylmethane | 0.50 |
| tocopheryl acetate | 0.50 |
| EDTA solution (20%) | 0.50 |
| NaOH | q.s. |
| ethyl alcohol | 1.50 |
| preservative | q.s. |
| perfume | q.s. |
| hydrophobic $TiO_2$ | 1.00 |
| fully demineralized water | to 100.00 |

EXAMPLE 3

Sun lotion, O/W

| | % by weight |
|---|---|
| trilaureth-4 phosphate | 0.75 |
| triceteareth-4 phosphate | 1.00 |
| glyceryl stearate + PEG-100 stearate | 1.00 |
| glyceryl stearate + ceteareth-20 | 0.80 |
| glyceryl lanolate | 0.50 |
| isopropyl palmitate | 3.00 |
| glycerol caprylate/caproate ("caprylic/capric triglyceride") | 5.00 |
| cetyl alcohol | 1.00 |
| xanthan gum | 0.30 |
| octyl methoxycinnamate | 6.00 |
| butylmethoxydibenzoylmethane | 0.50 |
| methylbenzylidenecamphor | 3.00 |
| phenylbenzimidazolesulphonic acid | 4.00 |

-continued

| | % by weight |
|---|---|
| butylated hydroxytoluene | 0.06 |
| EDTA solution (20%) | 0.50 |
| NaOH | q.s. |
| preservative | q.s. |
| hydrophobic $TiO_2$ | 3.00 |
| fully demineralized water | to 100.00 |

EXAMPLE 4

Sun lotion, O/W

| | % by weight |
|---|---|
| cyclomethicone | 2.00 |
| cetearyl alcohol + PEG-40-hydrogenated castor oil + sodium cetearyl sulphate | 2.50 |
| glyceryl lanolate | 1.00 |
| glycerol caprylate/caproate ("caprylic/capric triglyceride") | 2.00 |
| octyl stearate | 3.00 |
| castor oil | 4.00 |
| glycerol | 3.00 |
| Carbomer | 0.23 |
| hydroxypropylmethylcellulose | 0.30 |
| PVP/hexadecene copolymer | 1.50 |
| octyl methoxycinnamate | 4.00 |
| butylmethoxydibenzoylmethane | 2.00 |
| methylbenzylidenecamphor | 3.50 |
| butylated hydroxytoluene | 0.03 |
| EDTA solution (20%) | 0.50 |
| NaOH | q.s. |
| preservative | q.s. |
| perfume | q.s. |
| hydrophobic $TiO_2$ | 1.50 |
| fully demineralized water | to 100.00 |

EXAMPLE 5

Sun lotion, O/W

| | % by weight |
|---|---|
| stearic acid | 2.00 |
| cetyl palmitate | 1.00 |
| glycerol caprylate/caproate ("caprylic/capric triglyceride") | 2.00 |
| sorbitan monooleate | 1.00 |
| sorbitan monostearate | 1.50 |
| liquid paraffin DAB 9 | 1.29 |
| cetearyl alcohol | 0.80 |
| glycerol | 3.00 |
| 2-hydroxy-4-methoxybenzophenone | 1.00 |
| octyl methoxycinnamate | 5.00 |
| methylbenzylidenecamphor | 1.00 |
| butylated hydroxytoluene | 0.06 |
| simethicone | 0.20 |
| polyethylene glycol 150 | 3.00 |
| triethanolamine | 0.85 |
| Carbomer | 0.10 |
| ethyl alcohol | 3.00 |
| preservative | q.s. |
| perfume | q.s. |
| hydrophobic $TiO_2$ | 2.00 |
| fully demineralized water | to 100.00 |

EXAMPLE 6

Sun cream, O/W, sun protection factor 20

| | % by weight |
|---|---|
| cyclomethicone | 3.00 |
| glyceryl stearate + PEG-30 stearate | 2.00 |
| wool wax alcohol | 0.10 |
| glyceryl stearate | 3.00 |
| isopropyl palmitate | 2.00 |
| octyldodecanol | 1.00 |
| $C_{12-15}$alkyl benzoate | 2.00 |
| glycerol | 3.00 |
| cetyl alcohol | 3.00 |
| myristyl myristate | 2.00 |
| octyl methoxycinnamate | 4.50 |
| butylmethoxydibenzoylmethane | 2.00 |
| phenylbenzimidazolesulphonic acid | 3.00 |
| tocopheryl acetate | 0.50 |
| EDTA solution (20%) | 0.50 |
| NaOH (45%) | q.s. |
| ethyl alcohol | 4.00 |
| preservative | q.s. |
| perfume | q.s. |
| hydrophobic $TiO_2$ | 2.00 |
| cis-urocaninic acid | 0.25 |
| fully demineralized water | to 100.00 |

EXAMPLE 7

Sun cream, O/W, sun protection factor 8

| | % by weight |
|---|---|
| cyclomethicone | 3.00 |
| glyceryl stearate + PEG-30 stearate | 2.00 |
| glyceryl stearate | 3.00 |
| isopropyl palmitate | 2.00 |
| octyldodecanol | 3.00 |
| glycerol | 3.00 |
| cetyl alcohol | 3.00 |
| phenylbenzimidazolesulphonic acid | 1.00 |
| octyl methoxycinnamate | 5.00 |
| butylmethoxydibenzoylmethane | 0.50 |
| tocopheryl acetate | 0.50 |
| EDTA solution (20%) | 0.50 |
| NaOH | q.s. |
| ethyl alcohol | 1.50 |
| preservative | q.s. |
| perfume | q.s. |
| hydrophobic $TiO_2$ | 1.00 |
| urocaninic acid | 0.50 |
| fully demineralized water | to 100.00 |

EXAMPLE 8

Suntan lotion, O/W

| | % by weight |
|---|---|
| trilaureth-4 phosphate | 0.75 |
| tricetearoth-4 phosphate | 1.00 |
| glyceryl stearate + PEG-100 stearate | 1.00 |
| glyceryl stearate + ceteareth-20 | 0.80 |
| glyceryl lanolate | 0.50 |
| isopropyl palmitate | 3.00 |
| glycerol caprylate/caproate ("caprylic/capric triglyceride") | 5.00 |
| cetyl alcohol | 1.00 |
| zanthan gum | 0.30 |
| octyl methoxycinnamate | 6.00 |
| butylmethoxydibenzoylmethane | 0.50 |

-continued

| | % by weight |
|---|---|
| methylbenzylidenecamphor | 3.00 |
| phenylbenzimidazolesulphonic acid | 4.00 |
| butylated hydroxytoluene | 0.06 |
| EDTA solution (20%) | 0.50 |
| NaOH | q.s. |
| preservative | q.s. |
| urocaninic acid | 1.00 |
| hydrophobic $TiO_2$ | 3.00 |
| fully demineralized water | to 100.00 |

EXAMPLE 9

Sun lotion, O/W

| | % by weight |
|---|---|
| cyclomethicone | 2.00 |
| cetearyl alcohol + PEG-40-hydrogenated castor oil + sodium cetearyl sulphate | 2.50 |
| glyceryl lanolate | 1.00 |
| glycerol caprylate/caproate ("caprylic/capric triglyceride") | 2.00 |
| octyl stearate | 3.00 |
| castor oil | 4.00 |
| glycerol | 3.00 |
| Carbomer | 0.23 |
| hydroxypropylmethylcellulose | 0.30 |
| PVT/hexadecene copolymer | 1.50 |
| octyl methoxycinnamate | 4.00 |
| butylmethoxydibenzoylmethane | 2.00 |
| methylbenzylidenecamphor | 3.50 |
| butylated hydroxytoluene | 0.03 |
| EDTA solution (20%) | 0.50 |
| NaOH | q.s. |
| preservative | q.s. |
| perfume | q.s. |
| urocaninic acid | 0.25 |
| hydrophobic $TiO_2$ | 1.50 |
| fully demineralized water | to 100.00 |

EXAMPLE 10

Sun lotion, O/W

| | % by weight |
|---|---|
| stearic acid | 2.00 |
| cetyl palmitate | 1.00 |
| glycerol caprylate/caproate ("caprylic/capric triglyceride") | 2.00 |
| sorbitan monooleate | 1.00 |
| sorbitan monostearate | 1.50 |
| liquid paraffin, DAB 9 | 1.29 |
| cetearyl alcohol | 0.80 |
| glycerol | 3.00 |
| 2-hydroxy-4-methoxybenzophenone | 1.00 |
| octyl methoxycinnamate | 5.00 |
| methylbenzylidenecamphor | 1.00 |
| butylated hydroxytoluene | 0.06 |
| simethicone | 0.20 |
| polyethylene glycol 150 | 3.00 |
| triethanolamine | 0.85 |
| Carbomer | 0.10 |
| ethyl alcohol | 3.00 |
| preservative | q.s. |
| perfume | q.s. |
| urocaninic acid | 1.50 |
| hydrophobic $TiO_2$ | 2.00 |
| fully demineralized water | to 100.00 |

| Example | 11 | 12 | 13 | 14 |
|---|---|---|---|---|
| soya oil | 54.0 | 40.0 | 37.0 | 42.0 |
| castor oil | 14.0 | 14.0 | 9.0 | 14.0 |
| ZETESOL 100 | 30.0 | 51.0 | 51.0 | 41.0 |
| poloxamer 101 | 2.0 | 2.0 | 2.0 | 2.0 |
| hydrophobic $TiO_2$ | 2.5 | 2.5 | 2.5 | 2.5 |
| perfume, antioxidants, preservatives | q.s. | q.s. | q.s. | q.s. |

| Example | 15 | 16 | 17 | 18 |
|---|---|---|---|---|
| wheatgerm oil | 54.0 | 40.0 | 37.0 | 42.0 |
| castor oil | 14.0 | 14.0 | 9.0 | 14.0 |
| ZETESOL 100 | 30.0 | 51.0 | 51.0 | 41.0 |
| poloxamer 101 | 2.0 | 2.0 | 2.0 | 2.0 |
| hydrophobic $TiO_2$ | 2.5 | 2.5 | 2.5 | 2.5 |
| perfume, antioxidants, preservatives | q.s. | q.s. | q.s. | q.s. |

| Example | 19 | 20 | 21 | 22 |
|---|---|---|---|---|
| sunflower oil | 54.0 | 40.0 | 37.0 | 42.0 |
| castor oil | 14.0 | 14.0 | 9.0 | 14.0 |
| ZETESOL 100 | 30.0 | 51.0 | 51.0 | 41.0 |
| poloxamer 101 | 2.0 | 2.0 | 2.0 | 2.0 |
| hydrophobic $TiO_2$ | 2.5 | 2.5 | 2.5 | 2.5 |
| perfume, antioxidants, preservatives | q.s. | q.s. | q.0. | q.s. |

Comparison Example 1

Sun lotion, O/W

| | % by weight |
|---|---|
| stearic acid | 2.00 |
| cetyl palmitate | 1.00 |
| glycerol caprylate/caproate ("caprylic/capric triglyceride") | 2.00 |
| sorbitan monooleate | 1.00 |
| sorbitan monostearate | 1.50 |
| liquid paraffin, DAB 9 | 1.29 |
| cetearyl alcohol | 0.80 |
| glycerol | 3.00 |
| butylated hydroxytoluene | 0.06 |
| simethicone | 0.20 |
| polyethylene glycol 150 | 3.00 |
| triethanolamine | 0.85 |
| Carbomer | 0.10 |
| ethyl alcohol | 3.00 |
| preservative | q.s. |
| perfume | q.s. |
| fully demineralized water | to 100.00 |

Proof of action

The properties of the suntan lotion of Example 5 (stl 1) were tested against those of the $TiO_2$-free, but otherwise identical preparation of Comparison Example 1 (stl 2).

Using an LS 50 fluorescence spectrometer (Perkin Elmer), the reflection spectra of eight subjects were measured before and after treatment of the volar forearms with the test preparations and after bathing the forearms for 20 minutes. Urocaninic acid shows absorption at 308 nm; accordingly, a weak reflection peak at this wavelength suggests a relatively high urocaninic acid concentration.

After washing and in comparison with the "normal state", i.e. in comparison with before washing, the peak maximum at 308 nm increased by 46.3% in the case of stl 2, and by 29.7% in the case of stl 1.

This shows that the urocaninic acid concentration remaining on or in the skin must be considerably higher when using stl 1 than when using stl 2.

We claim:

1. In the method of preserving the urocaninic acid state of the skin by preventing the leaching out or washing off of the skin's cis- or trans-urocaninic acid from the human skin, caused by the action of water, or the leaching out or washing off of the skin's cis- or trans-urocaninic acid, which has been applied artificially to the skin, from the human skin caused by the action of water, the improvement which comprises applying to said skin a cosmetic or dermatological preparation containing a hydrophobicized pharmaceutically or cosmetically acceptable pigment, wherein the pigment is an inorganic metal oxide pigment or a mixture of inorganic metal oxide pigments wherein said metal is selected from the group consisting of titanium, zinc, iron, zirconium, silicon, manganese, aluminum and cerium.

2. The method according to claim 1, wherein the pigment is selected from the group consisting of $TiO_2$, ZnO, an iron oxide, $ZrO_2$, $SiO_2$, a maganese oxide, $Al_2O_3$, a cerium oxide and mixtures thereof.

3. The method according to claim 1, wherein the preparation comprises 0.01% to 30% by weight based upon the total weight of the formulation of inorganic pigments.

4. The method according to claim 1, wherein the preparation comprises 0.1% to 6% by weight, based upon total weight of the formulation, of inorganic pigments.

5. The method according to claim 1, wherein the preparation additionally comprises 0.00001 mg/ml to 60 mg/ml of urocaninic acid, based upon total volume of the preparation.

6. The method according to claim 1, wherein the preparation additionally comprises 0.05 mg/ml to 1.0 mg/ml of urocaninic acid, based upon total volume of the preparation.

7. The method according to claim 1, wherein the preparation is a sun screen preparation.

8. The method according to claim 1, wherein the preparation is a bath oil.

* * * * *